US008277837B2

(12) United States Patent
Fischer et al.

(10) Patent No.: US 8,277,837 B2
(45) Date of Patent: Oct. 2, 2012

(54) HEMOSTATIC TEXTILE (75) Inventors: Thomas H. Fischer, Hillsborough, NC (US); E. Stan Eskridge, Jr., Chapel Hill, NC (US); William M. Malloy, Jr., Cheraw, SC (US); Malloy Evans, Cheraw, SC (US)

(73) Assignees: Entegrion, Inc., Research Triangle Park, NC (US); University of North Carolina at Chapel Hill, Chapel Hill, NC (US)

( * ) Notice: Subject to any disclaimer, the term of this patent is extended or adjusted under 35 U.S.C. 154(b) by 1358 days.

(21) Appl. No.: 11/650,670

(22) Filed: Jan. 8, 2007

(65) Prior Publication Data
US 2007/0160653 A1 Jul. 12, 2007

Related U.S. Application Data (60) Provisional application No. 60/758,261, filed on Jan. 11, 2006.

(51) Int. Cl.
*A61F 13/00* (2006.01)
*A61K 38/17* (2006.01)
*A61K 38/36* (2006.01)
*A61K 9/70* (2006.01)
*A61L 15/16* (2006.01)
*A61L 15/32* (2006.01)
*A61L 15/44* (2006.01)
*C07K 14/435* (2006.01)
*C07K 14/745* (2006.01)
*C12N 5/07* (2010.01)

(52) U.S. Cl. ........ 424/443; 424/422; 424/423; 424/445; 424/446; 424/447; 530/350; 530/380; 530/381; 530/382; 530/383; 530/384; 435/325; 514/13.5; 514/13.7; 602/42; 602/43; 602/48; 602/50

(58) Field of Classification Search ........................ None
See application file for complete search history.

(56) References Cited

U.S. PATENT DOCUMENTS

| | | | |
|---|---|---|---|
| 3,328,259 A | 6/1967 | Anderson et al. | |
| 3,419,006 A | 12/1968 | King et al. | |
| 3,709,221 A * | 1/1973 | Riely | 602/43 |
| 3,753,842 A * | 8/1973 | Pittman | 442/366 |
| 3,787,272 A * | 1/1974 | Nisbet et al. | 428/193 |
| 4,145,185 A | 3/1979 | Brinkhous et al. | |
| 4,173,131 A | 11/1979 | Pendergrass et al. | |
| 4,192,299 A | 3/1980 | Sabatano | |
| 4,287,087 A | 9/1981 | Brinkhous et al. | |
| 4,323,061 A | 4/1982 | Usukura | |
| 4,390,519 A | 6/1983 | Sawyer | |
| 4,427,651 A | 1/1984 | Stroetmann | |
| 4,453,939 A | 6/1984 | Zimmerman et al. | |
| 4,606,337 A | 8/1986 | Zimmermann et al. | |
| 4,616,644 A | 10/1986 | Saferstein et al. | |
| 4,721,618 A | 1/1988 | Giles et al. | |
| 4,994,367 A | 2/1991 | Bode et al. | |
| 5,651,966 A | 7/1997 | Read et al. | |
| 5,795,571 A * | 8/1998 | Cederholm-Williams et al. | 424/94.64 |
| 5,800,372 A | 9/1998 | Bell et al. | |
| 5,891,393 A | 4/1999 | Read et al. | |
| 5,902,608 A | 5/1999 | Read et al. | |
| 5,993,804 A | 11/1999 | Read et al. | |
| 6,015,618 A | 1/2000 | Orima | |
| 6,056,970 A * | 5/2000 | Greenawalt et al. | 424/426 |
| 6,113,948 A | 9/2000 | Heath et al. | |
| 6,361,551 B1 | 3/2002 | Torgerson et al. | |
| 6,638,296 B2 | 10/2003 | Levinson | |
| 6,723,497 B2 | 4/2004 | Wolkers et al. | |
| 6,762,336 B1 | 7/2004 | MacPhee et al. | |
| 6,770,478 B2 * | 8/2004 | Crowe et al. | 435/374 |
| 6,878,025 B2 | 4/2005 | Mead | |
| 6,891,077 B2 | 5/2005 | Rothwell et al. | |
| 6,897,348 B2 | 5/2005 | Malik | |
| 6,955,682 B2 * | 10/2005 | Luthra et al. | 606/213 |
| 7,335,508 B2 * | 2/2008 | Yayon et al. | 435/343 |
| 7,543,608 B2 | 6/2009 | Santens | |
| 7,549,281 B2 | 6/2009 | Kuwano et al. | |

(Continued)

FOREIGN PATENT DOCUMENTS

CN 1461827 A * 12/2003

(Continued)

OTHER PUBLICATIONS

Fischer et al. The design and testing of a dual fiber textile matrix for accelerating surface hemostasis. J Biomed Mater Res Part B: Appl Biomater 91B: 381-389, 2009.*
Rich et al. Use of the novel hemostatic textile Stasilon to arrest refractory retroperitoneal hemorrhage: a case report. J Medical Case Report 4: 20, 2010.*
Schumacher et al. New haemostatic textile stopped refractory bleeding in an aplastic anaemia patient. Haemophilia 14: 871-872, 2008.*
English translation of CN1461827; Yu, Ganggang; Dec. 2003;; translated pp. 1-4.*
"Thrombin", www.copewithcytokines.de/cope.cgi?key=Thrombin, Mar. 2003, 3 pages.*
Thrombin definition, medical-dictionary.thefreedictionary.com/thrombin; downloaded Apr. 20, 2012, 2 pages.*
Mukherjee, R.N. Radiation: a means of sterilization. IAEA Bulletin 17(6): 28-37, 1975.*

(Continued)

*Primary Examiner* — Bridget E Bunner
(74) *Attorney, Agent, or Firm* — Fish & Richardson P.C.

(57) ABSTRACT

The present invention is directed to a hemostatic textile, comprising: a material comprising a combination of glass fibers and one or more secondary fibers selected from the group consisting of silk fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers, acetate fibers; and combinations thereof; the hemostatic textile capable of activating hemostatic systems in the body when applied to a wound. Additional cofactors such as thrombin and hemostatic agents such as RL platelets, RL blood cells; fibrin, fibrinogen, and combinations thereof may also be incorporated into the textile. The invention is also directed to methods of producing the textile, and methods of using the textile to stop bleeding.

45 Claims, 5 Drawing Sheets

U.S. PATENT DOCUMENTS

| | | | |
|---|---|---|---|
| 7,931,637 B2 * | 4/2011 | Vournakis et al. | 604/389 |
| 2001/0041186 A1 * | 11/2001 | Greenspan et al. | 424/405 |
| 2002/0001624 A1 | 1/2002 | Braun et al. | |
| 2002/0015724 A1 | 2/2002 | Yang et al. | |
| 2002/0127265 A1 * | 9/2002 | Bowman et al. | 424/426 |
| 2002/0156498 A1 * | 10/2002 | Jo et al. | 606/213 |
| 2003/0054330 A1 | 3/2003 | Fischer et al. | |
| 2003/0056484 A1 | 3/2003 | Oda | |
| 2003/0082966 A1 * | 5/2003 | Menday et al. | 442/1 |
| 2003/0134120 A1 | 7/2003 | Kim et al. | |
| 2004/0101546 A1 * | 5/2004 | Gorman et al. | 424/445 |
| 2005/0238701 A1 | 10/2005 | Kleinwaechter | |
| 2005/0272161 A1 * | 12/2005 | Nichols et al. | 436/63 |
| 2006/0009721 A1 * | 1/2006 | Evans | 602/5 |
| 2007/0267159 A1 | 11/2007 | Zhao | |
| 2009/0053288 A1 | 2/2009 | Eskridge, Jr. et al. | |
| 2009/0117799 A1 | 5/2009 | Yoshida et al. | |
| 2009/0260173 A1 | 10/2009 | Martin Rivera et al. | |
| 2010/0093241 A1 | 4/2010 | Medoff | |
| 2010/0178829 A1 | 7/2010 | Kulkarni | |

FOREIGN PATENT DOCUMENTS

| | | |
|---|---|---|
| EP | 0188942 | 7/1986 |
| EP | 1 338 648 A1 | 8/2003 |
| EP | 0 642 301 B1 | 12/2003 |
| JP | 5200104 | 8/1993 |
| JP | 2005169103 | 6/2005 |
| WO | WO 97/28832 A1 | 8/1997 |
| WO | WO9907417 | 2/1999 |
| WO | WO 99/59647 A1 | 11/1999 |
| WO | WO9956798 | 11/1999 |
| WO | WO 03/020116 A1 | 3/2003 |
| WO | WO 03/102281 A1 | 11/2003 |
| WO | WO03102281 | 12/2003 |

OTHER PUBLICATIONS

Ramachandran et al. Studies on the acid resistance of E glass. J Am Ceramic Soc 63(1-2): 1-3, 1980.*

Fischer, Thomas H. et al., *Non-classical processes in surface hemostasis: mechanisms for the poly-N-acetyl glucosamine-induced alteration of red blood cell morphology and surface prothrombogenicity*, Biomedical Materials, vol. 3, pp. 1-9 (2008).

Fischer, Thomas H. et al., *Hemostatic properties of glucosamine-based materials*, Journal of Biomedical Materials, Part A, vol. 80, pp. 167-174 (2006).

Fischer, Thomas H. et al., *Mechanisms for the Interaction of Hemostatic Systems with Foreign Materials*, Nova Science Publishers, Inc., In: Trends in Biomaterial Research, pp. 1-19 (2006).

Fischer, Thomas H. et al., *Synergistic platelet integrin signaling and factor XII activation in poly-N-acetyl glucosamine fiber-mediated hemostasis*, Biomaterials, vol. 26, pp. 5433-5443 (2005).

Fischer, Thomas H. et al., *Evidence That Rehydrated, Lyophilized Red Blood Cells are Sufficiently Deformable for Normal Microcirculation Transit*, Microscopy Research and Technique, vol. 64, pp. 62-71 (2004).

Fischer, Thomas H. et al., *Comparison of Structural and Hemostatic Properties of the Poly-N-Acetyl Glucosamine Syvek Patch With Products Containing Chitosan*, Microscopy Research and Technique, vol. 63, pp. 168-174 (2004).

JP Official Action dated Jun. 15, 2012, Japanese Application No. 2008-550382, pp. 3.

Authorized Officer B. Siebum. Extended European Search Report in International Application No. PCT/US2007/000645, dated Jul. 9, 2012, 6 pages.

* cited by examiner

HEMOSTATIC TEXTILE

CROSS-REFERENCE TO RELATED APPLICATIONS

This application claims the benefit of U.S. Provisional Application Ser. No. 60/758,261 filed Jan. 11, 2006, which is incorporated by reference herein in its entirety.

BACKGROUND OF THE INVENTION

1. Field of the Invention

The present invention is directed to textiles, such as bandages, sutures, or fabrics, and more particularly to hemostatic textiles that include agents that can control bleeding rapidly and can be stored for long periods of time.

2. Description of the Related Art

Despite considerable progress in understanding pathophysiological processes involved in surface (topical) hemostasis, there remains a considerable unmet need for materials that can be applied to sites of hemorrhage to staunch bleeding. Traumatic injury is the leading cause of death for individuals under 44 years of age (Bozeman, W. Shock, Hemorrhage (2001)). Approximately half of the 100,000 deaths annually in the United States per year from traumatic injury, or 50,000 cases, are from exsanguinations, (Peng, R., Chang, C., Gilmore, D. & Bongard, F. Am Surg Vol. 64 950-4 (1998)) and about the same number of hemorrhaging patients survive after massive red blood cell transfusion (Vaslef, S., Knudsen, N., Neligan, P., and Sebastian, M. J. Trauma-Inj. Inf. Crit. Care Vol. 53 291-296 (2002)). Thus, approximately 100,000 patients are in critical need of hemorrhage control in the US each year. The situation is equally critical in combat casualty care; in a recent review of military casualties (Burlingame, B. DOD's experiences in Afghanistan Advanced Technological Applications for Combat Casualty Care 2002 Conference in www.usaccc.org (2002)), the control of non-compressible bleeding was identified as the single most important unmet need in military emergency medicine. The standard of care is frequently the application of a tourniquet to control "compressible" bleeding and then gauze to control the residual "noncompressible" bleeding. However, continued blood loss through gauze is a major contributor to morbidity and mortality.

The prior art is replete with patents directed to various forms of bandages. For example, U.S. Pat. No. 3,419,006 to King discloses a sterile transparent dressing for a wound and made from a hydrophilic polymeric gel of an insoluble polymer, and U.S. Pat. No. 4,323,061 to Usukura discloses a rigid bandage made from glass fibers and non-glass fibers. In addition, various methods have been attempted to quickly arrest bleeding in an injured person. Several of these methods include articles such as bandages supplemented with substances that chemically accelerate the body's natural clotting processes. Examples of such articles include the following:

U.S. Pat. No. 3,328,259 to Anderson discloses a bandage or wound dressing that incorporates polymers such as sodium carboxymethyl cellulose, hydroxyethyl cellulose, polyoxyethylene, polyvinylpyrrolidone, and the like.

U.S. Pat. No. 4,192,299 to Sabatano discloses a bandage that includes a packet containing an antiseptic substance.

U.S. Pat. No. 4,390,519 to Sawyer discloses a bandage in the form of a sponge and containing collagen or a collagen-like substance.

U.S. Pat. No. 4,453,939 to Zimmerman et al. discloses a composition useful as a wound dressing and made from a combination of collagen, fibrinogen and thrombin.

U.S. Pat. No. 4,606,337 to Zimmerman et al. discloses a resorptive sheet for closing and treating wounds, and composed of a glycoprotein matrix that contains fibrinogen and thrombin.

U.S. Pat. No. 4,616,644 to Saferstein et al. discloses an adhesive bandage that includes high molecular weight polyethylene oxide as a hemostatic agent.

U.S. Pat. No. 5,800,372 to Bell et al. discloses a dressing made from an absorbent polymer and includes microfibrillar collagen.

U.S. Pat. No. 5,902,608 to Read et al. discloses surgical aids such as bandages, gauzes, sutures, and the like, that contain fixed-dried blood cells that express platelet-derived growth factors.

U.S. Pat. No. 6,638,296 to Levinson discloses a bandage that includes a pad containing glucosamine or a glucosamine derivative.

U.S. Pat. No. 6,762,336 and International Patent Application Publication No. WO/99/59647 to MacPhee et al. discloses a multilayer bandage that includes a thrombin layer sandwiched between two fibrinogen layers.

U.S. Pat. No. 6,897,348 to Malik discloses an adhesive bandage that contains an antimicrobial agent and a hemostatic agent (e.g., chitosan, niacinamide, or ascorbic acid), or a single wound-healing agent that contains both antimicrobial and hemostatic activities (e.g., chitosan niacinamide ascorbate salt).

U.S. Pat. No. 6,891,077 to Rothwell et al. discloses fibrinogen bandages that include a procoagulant such as propyl gallate, gallic acid, or a derivative thereof. Optional ingredients such as thrombin or an antimicrobial agent may also be included.

International Patent Application Publication No. WO 97/28823 to New Generation Medical Corporation discloses a hemostatic bandage that contains powdered fibrinogen and thrombin adhered to a fibrous matrix with a viscous, nonaqueous adhesive such as a viscous polysaccharide, glycol, or petroleum jelly.

Despite considerable progress in understanding pathophysiological processes involved in hemostasis, tissue remodeling, and resolution at wound sites, there remains a critical unmet need for a material that can be applied to sites of injury to accelerate these processes. The present invention is believed to be an answer to that need.

SUMMARY OF THE INVENTION

In one aspect, the present invention is directed a hemostatic textile, comprising: a material comprising a combination of glass fibers and one or more secondary fibers selected from the group consisting of silk fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers, acetate fibers; and combinations thereof; the hemostatic textile capable of activating hemostatic systems in the body when applied to a wound.

In another aspect, the present invention is directed to A hemostatic textile, comprising: a material comprising a combination of about 65% by weight glass fibers and about 35% by weight raw or regenerated bamboo fibers; the hemostatic textile capable of activating hemostatic systems in the body when applied to a wound.

In yet another aspect, the present invention is directed to a hemostatic textile, comprising: a material comprising glass fibers and one or more secondary fibers selected from the group consisting of silk fibers; polyester fibers; nylon fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof; and thrombin or a fraction comprising thrombin; the hemostatic textile capable of activating hemostatic systems in the body when applied to a wound.

In yet another aspect, the present invention is directed to a hemostatic textile, comprising: a material comprising a combination of about 65% by weight glass fibers and about 35% by weight raw or regenerated bamboo fibers; and from about 0.1 to about 5% by weight of thrombin or a fraction comprising thrombin based on the total weight of the textile; the hemostatic textile capable of activating hemostatic systems in the body when applied to a wound.

In yet another aspect, the present invention is directed to a hemostatic textile, comprising: a material comprising glass fibers and one or more secondary fibers selected from the group consisting of silk fibers; polyester fibers; nylon fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof; and one or more hemostatic agents selected from the group consisting of RL platelets, RL blood cells; fibrin, and fibrinogen; the hemostatic textile capable of activating hemostatic systems in the body when applied to a wound.

In yet another aspect, the present invention is directed to a hemostatic textile, comprising: a material comprising a combination of about 65% by weight glass fibers and about 35% by weight raw or regenerated bamboo fibers; and one or more hemostatic agents selected from the group consisting of RL platelets, RL blood cells, fibrin, and fibrinogen, wherein the RL platelets and the RL blood cells comprise from about 0.1 to about 20 wt % and the fibrin and the fibrinogen comprise from about 0.1 to about 5 wt %, based on the total weight of the textile; the hemostatic textile capable of activating hemostatic systems in the body when applied to a wound.

In yet another aspect, the present invention is directed to a hemostatic textile, comprising: a material comprising glass fibers and one or more secondary fibers selected from the group consisting of silk fibers; polyester fibers; nylon fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof; and thrombin or a fraction containing thrombin; and one or more hemostatic agents selected from the group consisting of RL platelets, RL blood cells; fibrin, and fibrinogen; the hemostatic textile capable of activating hemostatic systems in the body when applied to a wound.

In yet another aspect, the present invention is directed to a hemostatic textile, comprising: a material comprising a combination of about 65% by weight glass fibers and about 35% by weight raw or regenerated bamboo fibers; from about 0.1 to about 5% by weight of thrombin or a fraction comprising thrombin based on the total weight of the textile; and one or more hemostatic agents selected from the group consisting of RL platelets, RL blood cells, fibrin, and fibrinogen, wherein the RL platelets and the RL blood cells comprise from about 0.1 to about 20 wt % and the fibrin and the fibrinogen comprise from about 0.1 to about 5 wt %, based on the total weight of the textile; the hemostatic textile capable of activating hemostatic systems in the body when applied to a wound.

In yet another aspect, the present invention is directed to a method of preparing a hemostatic textile, comprising the steps of: (1) contacting a material comprising glass fibers and one or more secondary fibers selected from the group consisting of silk fibers; polyester fibers; nylon fibers; ceramic fibers; raw or regenerated bamboo fibers; cotton fibers; rayon fibers; linen fibers; ramie fibers; jute fibers; sisal fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof with thrombin or a fraction comprising thrombin and optionally a hemostatic agent selected from the group consisting of RL platelets, RL blood cells; fibrin, fibrinogen, and combinations thereof; to form a wet matrix; and (2) drying the wet matrix to produce the hemostatic textile.

In yet another embodiment, the present invention is directed to a method of preparing a hemostatic textile, comprising the steps of: (1) contacting a material comprising glass fibers and one or more secondary fibers selected from the group consisting of silk fibers; polyester fibers; nylon fibers; ceramic fibers; raw or regenerated bamboo fibers; cotton fibers; rayon fibers; linen fibers; ramie fibers; jute fibers; sisal fibers; flax fibers; soybean fibers; corn fibers; hemp fibers; lyocel fibers; wool; lactide and/or glycolide polymers; lactide/glycolide copolymers; silicate fibers; polyamide fibers; feldspar fibers; zeolite fibers, zeolite-containing fibers; acetate fibers; and combinations thereof with platelet rich plasma containing platelets; (2) crosslinking the platelets; and (3) optionally contacting the textile with thrombin or a fraction comprising thrombin to produce the hemostatic textile.

These and other aspects will become apparent upon reading the following detailed description of the invention.

BRIEF DESCRIPTION OF THE FIGURES

The invention will be better understood when taken in conjunction with the following figures in which.

DETAILED DESCRIPTION OF THE INVENTION

The inventors of the present invention have unexpectedly found that a hemostatic textile can be prepared from a composite of glass fibers and one or more secondary fibers. The hemostatic textile made from the composite of fibers displays excellent hemostatic properties and fluid absorbency. To further enhance the hemostatic properties of the hemostatic textile made from the composite, additional blood factors such as thrombin, lyophilized blood cells, lyophilized platelets, fibrin, fibrinogen, or combinations of these, may be added. These additional factors aid in activating the body's natural hemostasis cascade and result in a material that can rapidly arrest bleeding. The inventors have discovered that the combination of glass fibers, secondary fibers, and additional blood factors produce a novel hemostatic textile that rapidly arrests bleeding, and is useful in situations where large hemorrhages exist or when a patient cannot be immediately admitted to a hospital or trauma treatment center.

The hemostatic textile of the present invention provides important advantages over current products that activate hemostasis. The present invention is capable of rapidly activating the body's natural hemostatic systems, such as the blood coagulation cascade, by providing locally high concentrations of substances that activate that cascade. In addition, by using lyophilized blood proteins, the hemostatic textile of the present invention may be stored in a dry state ready for immediate use for long periods of time. This aspect is particularly advantageous because previous products and systems required hydrated proteins for activation.

As indicated above, one embodiment of the present invention is a hemostatic textile matrix, comprising a material comprising a combination of glass fibers and one or more secondary fibers. Each of these components is discussed in more detail below.

The glass fiber component is preferably a fiberglass prepared by extrusion or electrospinning processes, and has fiber diameters from 5 nanometers to 15 microns. Types of glass contemplated for use in the present invention include but are not limited to alumino-borosilicate glasses with low sodium oxide content, borosilicate glass, lead glass, aluminosilicate, alkali-barium silicate, vitreous silica, chalcogenide glass, phosphate glass, and bioactive glass sold under the trade name "BIOGLASS". The dimensions of the glass fiber component may be described by conventional nomenclature, including the following designations: B (3.5 micron diameter); C (4.5 micron diameter); D (5 micron diameter); DE (6 micron diameter); E (7 micron diameter); G (9 micron diameter); H (10 micron diameter); or K (13 micron diameter). In addition, strand count of the glass fiber component can range from 900 to 37. The grade of the glass fiber may be any of electrical grade ("E"), chemical grade ("C"), or high strength ("S"), and the filaments may be in any arrangement, for example continuous, staple, or textured. The fiberglass fibers may also be used singly or in a plied state using 2 to 20 or more fibers. Fiberglass material is available commercially from various suppliers such as Owens Corning, and is available commercially as Grades G75, E-grade fiberglass, and the like, using the designations described above.

Secondary fibers used in the textile of the invention include generally any other fiber that can be combined with the glass fibers to impart absorbency, softness, and additional hemostatic activity to the textile. As explained in more detail below, use of secondary fibers with excellent absorbency also aids in incorporating additional hemostatic factors to the textile. Examples of useful secondary fibers include, but are not limited to, silk fibers; polyester fibers; nylon fibers; ceramic fibers; polysaccharide fibers including plant fibers such as raw or regenerated (e.g., chemically processed) bamboo, cotton, rayon, linen, ramie, jute, sisal, flax, soybean, corn, hemp, and lyocel; animal fibers such as wool; lactide and/or glycolide polymers; lactide/glycolide copolymers; silicate fibers; polyamide fibers; feldspar fibers; zeolite fibers, zeolite-containing fibers; acetate fibers; plant fibers that have been genetically engineered to express mammalian coagulation proteins or mammalian vasoactive factors. Other secondary fibers that are suitable for use in the present invention are fibers that have been covalently modified with polymers to promote water absorbancy (e.g., polyvinyl alcohols) and polymers that contain molecular moieties that activate hemostatic systems (e.g., linear or cyclized-arginine-glycine-aspartate-moieties such as those found in eptifibatide). Preferred secondary fibers include plant fibers such as raw or regenerated (e.g., chemically processed) bamboo fibers, cotton fibers, and the like, that have high moisture absorbancy and that are capable of activating the intrinsic coagulation cascade. The secondary fibers may be prepared using conventional methods, including ring, open end (OE), rotor, or air jet spinning, and may have counts ranging from 1/1 to 100/1 Ne.

As will be appreciated by one of skill in the art, the secondary fibers may be used singly, or in combinations of two, three, four, or more in a blended or plied state. In addition, any type of combination of secondary fibers may be used. For example, in one embodiment, two or more secondary fibers may be individually produced and then blended or plied together to form a composite yarn. In another embodiment, the secondary fibers may be formed as a conjugate comprising blocks of the selected types of fibers, for example alternating blocks of polyesters and polysaccharides. In yet another embodiment, the secondary fibers may be formed as a homogeneous combination of different threads.

The relative amounts of glass fibers and secondary fibers can range widely, for example from about 0.1 to 99.9 wt % glass fibers and about 99.9% to 0.1% by weight secondary fibers, based on the total weight of the dried textile. Preferable amounts of these materials range from about 30 to 80 wt % glass fibers and about 70 to 20 wt % secondary fibers, and more preferably from about 50 to 80 wt % glass fibers to about 50 to 20 wt % secondary fibers. Examples of useful proportions of glass and secondary fibers in the hemostatic textile of the invention include about 50 wt % glass fibers and about 50 wt % secondary fibers; about 40 wt % glass fibers and about 60 wt % secondary fibers; about 30 wt % glass fibers and about 70 wt % secondary fibers; or about 20 wt % glass fibers and about 80 wt % secondary fibers. One particularly useful combination is about 65% by weight glass fibers and 35% by weight bamboo fibers. The glass fiber component and the secondary fiber component may be combined using conventional methods such as spinning, weaving or knitting, or may be used in a nonwoven state.

In use, the hemostatic textile of the invention may take any configuration. In one embodiment, the hemostatic textile consists of a hemostatic layer designed to accelerate hemostasis, and an outer layer designed for surface texture, moisture transfer, fluid adsorption and microbial protection. In another embodiment, the hemostatic textile consists of three layers: a hemostatic layer designed to accelerate hemostasis, a middle layer for bandage strength and elasticity, and an outer layer for designed for surface texture, moisture transfer, fluid adsorption and microbial protection. Additional configurations may be conceived by those of skill in the art.

The hemostatic textile of the invention may also be treated with various agents that enhance its effectiveness. Examples of additional agents include organic or inorganic compounds that are microstatic or microcidal; organic or inorganic compounds that covalently react with blood coagulation proteins; organic or inorganic compounds that covalently react with wounded tissue to form covalent bonds for enhanced adhesion to tissues; organic or inorganic compounds that polymerize to form a three-dimensional polymer network at or on the wound; imaging agents such as ultrasound contrast agents (e.g., gas-filled microbubbles, metallic nanoparticles, and the like), radio-opaque agents (e.g., iodinated small molecules such as iopromide, iodinated high molecular weight polymers, and the like), magnetic resonance probes (e.g., ferumoxide iron nanoparticles, superparamagnetic metallic nanoparticles, diethylenetriaminepentaacetate (DTPA)-chelated gadolinium, and polymers that contain DTPA-chelated gadolinium, and the like).

Further additional agents that may be included in the hemostatic textile of the invention include skin conditioners such as aloe vera, vitamin E, coenzyme Q, collagen, and the like; anti-inflammatory agents such as aspirin, ibuprofen, acetominophen, vitamin C, COX-2 inhibitors, steroids, and the like; analgesics such as lidocaine, tetrocaine, opiates, cocaine, antihistamines, and the like; antimicrobial or antifungal agents such as bacitracin, silver salts, iodide, and the like; vasoconstrictors such as epinepherine, norepinephrine, vasopressin, hemoglobin, endothelins, thromboxanes, NO scavengers, and the like; growth factors such as MMP inhibitors, PDGF, and the like; anti-scar agents such as IL-11, anti-kheloid compounds, and the like; cauterizing agents that undergo an exothermic reaction upon rehydration such as zeolites; dehydrating agents that are hydroscopic such dextran; prothrombotic agents, such as zeolite, dextran sulfate, polyphosphate, mineral interfaces, phosphatidyl serine, calcium, and the like.

The textile matrix of the invention may also include additional factors that act to activate the body's natural hemostatic systems and thus aid in quickly arresting bleeding. Such additional factors include thrombin or a plasma fraction that includes thrombin, rehydrated lyophilized (RL) platelets, RL blood cells, fibrin, fibrinogen, and combinations of these. In one preferred embodiment, thrombin is incorporated into the textile to impart additional hemostatic action. The thrombin can be from any source (naturally isolated, recombinant, etc.) or may be in the form of a plasma fraction or serum that contains thrombin and additional coagulation factors such as factor XII, factor XIIa, factor XI, factor XIa, factor XIII, factor XIIIa, factor IX, factor IXa, factor VIII, factor VIIa, factor vWF, factor V, factor Va, factor X, factor Xa, and combinations thereof, or other coagulation cofactors such as components of animal venom, such as reptilase, or vasoactive agents such as endothelins, thromboxanes, nitrous oxide (NO) scavengers, or combinations thereof. These factors, or any of the factors listed above, may be in a dry or liquid form when incorporated into the textile of the invention.

The thrombin contemplated for use in the textile of the invention may take any form including highly purified thrombin IIa from human or animal sources, genetically modified plants, or other natural or recombinant protein expression systems. In addition, partially purified thrombin from human or animal sources, genetically modified plants, or other natural or recombinant protein expression systems may be used in the present invention. The thrombin contemplated for use in the present invention may also be contained in purified or partially purified serum or plasma. In one embodiment, the thrombin used in the textile of the present invention is a partially purified serum fraction containing thrombin IIa.

The preferred amount of thrombin in the textile of the invention ranges from about 0.01% by weight to about 10% by weight, based on the total weight of the dry textile. More preferred amounts of thrombin included in the textile of the invention range from about 0.05% by weight to about 7% by weight, and most preferably from about 0.1% by weight to about 5% by weight, all based on the total weight of the dry textile.

As explained in more detail in the Examples below, to produce a hemostatic textile that includes thrombin, the textile matrix is soaked in a solution containing thrombin, and frozen and lyophilized. Preservatives such as glycerol, propanediol, polyoxyethylene glycol (PEG) trehalose, and the like, may be included in the soaking solution to prevent the textile from becoming brittle or chalky during lyophilization. In general, preservative concentrations in the thrombin solution range to a maximum of about 20% (v/v). In preferred embodiments, about 12% (v/v) glycerol is used.

In another preferred embodiment, one or more of rehydrated lyophilized (RL) platelets, RL blood cells, fibrin or fibrinogen are incorporated into the textile to impart additional hemostatic action. Rehydrated lyophilized blood cells and rehydrated platelets and methods of their manufacture are known in the art. See, for example, U.S. Pat. Nos. 4,287,087; 5,651,966; 5,891,393; 5,902,608; 5,993,804; all incorporated by reference herein. Briefly, RL platelets are made by isolating the platelets, exposing them to a fixative such as formaldehyde, and drying. RL platelets may also be purchased commercially from Entegrion, Inc. (Research Triangle Park, N.C.) under the trade name "STASIX". Methods of isolation and purification of fibrin and fibrinogen are also known in the art.

Briefly, to produce RL blood cells, blood can be obtained from healthy volunteers, following signed informed consent, in citrate-phosphate-dextrose with adenine (CPDA-1) and subjected to centrifugation at 1000×g for 20 min to obtain RBCs. The erythrocytes are diluted to a hematicrit=5% in phosphate buffered saline (PBS) and centrifuged at 2,000×g for 10 min. This step can be repeated two additional times to separate RBCs from plasma proteins. RBCs may then be cross-linked with glutaraldehyde (for glut-RL RBCs) or a mixture of paraformaldehyde and glutaraldehyde (for para-RL RBCS). Unreacted aldehyde can be removed from the RBCs by centrifugation (as for the removal of the cells from plasma proteins), and finally the cells are frozen and lyophilized at −30° C.

Fibrin and fibrinogen are also available commercially from various sources. For example, clinical grade material is sold under the tradename HAEMOCOMPLETTAN P from ZLB Behring (Marburg, Germany) and TISSEEL from Baxter (Deerfield, Ill. USA). Research grade material is available from Enzyme Research Laboratories (South Bend, Ind. USA). Fibrin and fibrinogen may also be isolated according to procedures known in the art (e.g., van Ruijven-Vermeer I A, et al., Hoppe Seylers Z Physiol Chem. 360:633-7 (1979)). Fibrin and fibrinogen may also be isolated using glycine, ammonium sulfate, or ethanol precipitations that are known in the art.

The RL platelets, RL blood cells, fibrin, or fibrinogen, may be added in powder form by sprinkling or blowing the dried material onto the matrix and freeze-drying. Alternatively, these materials may be added to the matrix in solution form, and frozen and dried as described above. Preservatives such as glycerol, propanediol, polyoxyethylene glycol (PEG) trehalose, and the like, may be included in the soaking solution to prevent the textile from becoming brittle or chalky during lyophilization. In general, preservative concentrations in the thrombin solution range to a maximum of about 20% (v/v). In preferred embodiments, 12% (v/v) glycerol is used.

Any combination of RL blood cells, RL platelets, fibrin and/or fibrinogen may be incorporated into the textile of the present invention. Preferably, the total amount of RL blood cells, RL platelets, fibrin and/or fibrinogen ranges from about 0.1% to about 50% based on the total weight of the dried textile. In exemplary embodiments, the hemostatic textile of the invention may include the following combinations (all weight percents are expressed based on the total weight of the dried textile):

| Range | RL Platelets or RL Blood Cells (wt %) | Fibrin or Fibrinogen (wt %) |
|---|---|---|
| Preferred Range | 0.1 to 20 | 0.1 to 5 |
| More Preferred Range | 1.0 to 10 | 0.5 to 2 |
| Most Preferred Range | 3 to 7 | 0.75 to 1.5 |

In yet another embodiment, the textile matrix of the invention includes both thrombin or a fraction containing thrombin and one or more of rehydrated lyophilized (RL) platelets, RL blood cells, fibrin or fibrinogen. For example, one preferred combination of dried platelets, fibrinogen and thrombin is about 3 to 7 wt % RL platelets, 0.75 to 1.5 wt % fibrinogen, and 0.1 to 5 wt % thrombin, all based on the total weight of the dried textile. In one particularly preferred embodiment, a combination of about 5 wt % RL platelets, about 1 wt % fibrinogen, and about 0.1 wt % thrombin is used.

A hemostatic textile that contains both thrombin and one or more of rehydrated lyophilized (RL) platelets, RL blood cells, fibrin or fibrinogen is preferably made by first incorporating thrombin into the matrix followed by incorporation of one or more of rehydrated lyophilized (RL) platelets, RL blood cells, fibrin or fibrinogen using the techniques described generally above. In one embodiment, the hemostatic textile of the invention may be infused with a combination of fibrinogen and thrombin as disclosed in U.S. Pat. No. 6,113,948, incorporated herein by reference, and available from ProFibrix BV (Leiderdorp, The Netherlands) under the trade name "FIBROCAPS" (a combination of fibrinogen microspheres and thrombin microspheres). Preservatives such as glycerol, propanediol, polyoxyethylene glycol (PEG) trehalose, and the like, may be included in the soaking solution to prevent the textile from becoming brittle or chalky during lyophilization. In general, preservative concentrations in the thrombin solution range to a maximum of about 20% (v/v). In preferred embodiments, 12% (v/v) glycerol is used.

Generally, the hemostatic textile of the invention is made by the following steps:

1. RL platelets or RL blood cells are prepared and lyophilized according to published procedures;
2. The hemostatic textile is manufactured from textile components. During this step, the textile may be treated chemically by addition of a defined amount of agents such as glycerol, propanediol, polyoxyethylene glycol (PEG) to preserve the textile and aid in adhesion of hemostatic proteins. Additionally, in this step, thrombin-containing serum or plasma is freeze-dried onto the textile matrix.
3. Hemostatic proteins such as RL platelets, RL blood cells, fibrin, or fibrinogen are applied directly to a selected surface of the hemostatic textile (e.g., a surface that will contact wounded tissue) at a pre-selected particle density (protein per square area of textile surface) or weight percentage based on the total weight of the textile. The hemostatic proteins may be applied in any order, and may be applied to the textile in solution form or in a dry form. In one embodiment, RL platelets may be aldehyde-stabilized, applied to the textile in a liquid state, and then freeze dried onto the textile.
4. The infused hemostatic textile is packaged and optionally subjected to sterilization (e.g., gamma or UV irradiation).

Detailed examples of hemostatic textiles and their method of manufacture are outlined below.

The textile matrix of the invention is capable of activating hemostatic systems in the body when applied to a wound, including the blood coagulation systems and vasoconstriction systems. It has long been known that various materials activate platelets and other blood coagulation factors when they come into contact with a wound site. Platelets, as a primary cellular component of blood that provide hemostasis in response to vascular injury, become contact-activated when exposed to foreign materials such as metals glass, and plastics. See, for example, Barr, H. The stickiness of platelets. *Lancet* ii, 775 (1941)). In addition, it is well known that thrombin converts fibrinogen to fibrin in the blood clotting cascade. The combination of components in the hemostatic textile of the present invention act together locally and synergistically to activate the blood coagulation cascade in a highly concentrated and localized form when applied to a wound.

The hemostatic textile of the invention is useful as a wound dressing, for example, a bandage, gauze, and the like, or may be shaped into sutures for use in surgery. Additional uses include forming the hemostatic textile of the invention into fabrics for use in the manufacture of protective clothing or liners for clothing, or for use in tourniquets. Additionally, in another embodiment, the hemostatic textile of the present invention is in the form of a kit for use in surgery or emergency or trauma situations. The kit includes the hemostatic textile of the invention in rolls, sheets, or other appropriate shape, and may be used with or without the additional blood factors.

EXAMPLES

The following examples are intended to illustrate, but in no way limit the scope of the present invention. All parts and percentages are by weight and all temperatures are in degrees Celsius unless explicitly stated otherwise.

Materials

The following solutions were used in the Examples described below.

Anticoagulant Citrate Dextrose (ACD): 0.042 M $Na_3$Citrate, 0.035 M citric acid, 20% (w/v) anhydrous dextrose, pH to 4.5.

Citrated Saline: 6.2 mM $Na_3$Citrate, 150 mM NaCl, pH 6.5.

Imidazole Buffered Saline: 84 mM imidazole, 150 mM NaCl, pH 6.8.

4% Paraformaldehyde: 20 grams paraformaldehyde and 9.4 grams $NaH_2PO_4$ are suspended in 400 ml deionized $H_2O$ and heated to about 60° C. in a water bath until dissolved. pH is set to 7.2 and water is added to 500 ml.

Fixative Solution (prepared immediately before use): Combine 1 ml ACD, 10 ml 0.135 Molar $NaH_2PO_4$, pH=6.5, and 9 ml 4% (w/v) paraformaldehyde.

Imidazole Buffer: 84 mM imidazole, pH=6.8

Citrate Stock: 3.2% sodium citrate, pH=7.4

Examples 1-7

Preparation of Hemostatic Textiles

The following specific textile combinations was made and used in the experiments that follow:

Textile 1: Woven style; G75 fiberglass in warp; 30/1 100% Bamboo Rayon OE in the Fill The above combination was a glass fiber/bamboo co-weave with the glass fibers (G75, electronic grade E225 spun yarn from E-grade extruded glass) in the "long" orientation (warp) and the bamboo fibers running "across" the fabric (fill).

Textile 2: Woven Style; ECBC150 1/0 1.0 Z Fiberglass in warp; 18/1 100% Bamboo Rayon MJS in the fill.

Textile 3: Woven Style; ECE225 2/0 4.0 Z Fiberglass in warp; 18/3 100% Bamboo Rayon RS in the fill.

Textile 4: Knit Style; 1 end—ECG75 1/2 Fiberglass; 1 end—18/1 100% Bamboo Rayon OE in the fill.

Textile 5: Knit Style; 2 Ply—ECG150 1/0 Fiberglass twisted with 20/1 100% Bamboo Rayon.

Textile 6: Woven Style; ECE225 2/0 4.0 Z Fiberglass in warp; 16/2 100% Flax in the fill.

Textile 7: Woven Style; ECH18 1/0 0.7 Z Fiberglass in warp; 18/2 100% Lyocel MJS in the fill.

Example 8

Preparation of a Hemostatic Textile Matrix that Includes Thrombin 120 mg angel hair grade glass fiber was combined with 8 ml plasma (Innovative Research, Inc., Southfield, Mich.) and 80 µl of 1M $CaCl_2$ and placed on rocker. The mixture was mixed gently on the rocker for about 90 minutes, and the glass fiber separated from the mixture by centrifugation (300×g for 5 minutes). The supernatant was collected and glycerol was added to a final concentration of 9% by weight. The final product is a serum that contains thrombin IIa.

50 $cm^2$ of Textile 1 above was soaked for about 1 minute in approximately 5 ml of the above serum. Excess serum was allowed to drain off, and the soaked textile matrix was frozen at −20° C. and lyophilized.

Example 9

Preparation of a Hemostatic Textile Matrix that includes Thrombin and an additional Hemostatic Agent A. Textile Matrix that includes Thrombin and Rehydrated Lyophilized (RL) Platelets Two methods for preparing textile-based hemostatic matrixes with rehydrated lyophilized (RL) platelets and thrombin are detailed here. The quality of preparations may be evaluated using the Thrombin Generation Analysis described below.

1. Method 1

In this method, RL platelets are manufactured separately, then added to the textile matrix.

(a). Preparation of RL Platelets

RL platelets are prepared as described in U.S. Pat. Nos. 5,651,966 and 6,139,878, herein incorporated by reference. Alternatively, the following procedure may be used:

Platelet rich plasma (PRP) is prepared by first drawing fresh venous blood into ACD (e.g., 42.5 ml blood into 7.5 ml ACD in a 50 cc syringe). The blood is subjected to centrifugation (10 minutes, 1,200 rpm at 25-27° C.) to layer the red blood cells. The PRP is found in the supernatant. Alternatively, PRP can be isolated from stored and/or outdated platelets by removing the cells from the storage bag and centrifuging for 10 minutes at about 1200 rpm to remove contaminating red blood cells and aggregated platelets.

Plasma proteins are removed from PRP using centrifugation (10 minutes at about 2400 rpm), and resuspending the isolated platelets in citrated saline buffer. The platelets are washed twice in citrated saline buffer, and resuspended in citrated saline buffer to a final concentration of about $8\times10^9$ platelets/ml. Alternatively, plasma proteins may be removed from PRP using sizing chromatography (Sepharose 4B equilibrated with citrated saline buffer). Turbid fractions can be collected, combined, and platelets isolated by centrifugation. The platelets are then resuspended in citrated saline buffer to a final concentration of about $8\times10^9$ platelets/ml.

The isolated platelets are cross-linked by adding dropwise 3.5 ml of fixative solution to 1.25 ml of isolated platelets at a concentration of about $8\times10^9$ platelets/ml with gentle stirring. Fixative solution is added to a final volume of about 10 ml, and the mixture is incubated for 1 hour at room temperature without stirring or agitation. The cross-linked platelets are isolated by centrifugation (10 min at 2400 rpm), and resuspended in imidazole buffered saline, washed, and finally resuspended in imidazole buffered saline to a final concentration of about $1\times10^9$ platelets/ml.

The crosslinked platelets are frozen and lyophilized by first suspending them in imidazole buffered saline with 5% bovine serum albumin at pH 6.8 to a final platelet concentration of about $0.8\times10^9$ platelets/ml. The mixture is distributed into 1 ml aliquots, frozen at −80° C., and lyophilized overnight or longer. The lyophilized product may be stored at −20° C. The lyophilized cross-linked platelets may be rehydrated by resuspending in imidazole buffer.

(b). Addition of RL platelets to a Matrix.

To prepare a matrix that contains RL platelets, RL platelets are first milled in the dry state to a fine powder. The fine powder is sprinkled evenly onto a flat sterile surface, such as a Petri dish and one side of the freeze-dried thrombin-loaded matrix prepared in Example 8 above is pressed onto the RL powder and removed. The powdered RL platelets may also be blown into the textile using known blowing techniques. As an alternative method, RL platelets can be prepared without freeze-drying and in the absence of serum albumin, and resuspended in the thrombin serum prepared in Example 8 above. Soaking the desired matrix in this solution produces the final product. As a second alternative, rehydrated RL platelets can be resuspended in the thrombin serum described in Example 8 above and used to soak the desired matrix to product the final product.

2. Method 2

In this method, the RL platelets are aldehyde-stabilized after binding to the textile matrix, as a component of the matrix. The principle here is to first allow the platelets to contact-activate and adhere to the matrix through normal interactive processes between the hemostatic cells and the textile fibers. The platelets and textile matrix is then taken through the aldehyde stabilization process together. This method includes the following steps:

(a) Platelet rich plasma (PRP) is prepared as described above or alternatively obtain normally liquid stored platelet rich plasma.

(b) The platelet rich plasma is incubated with a quantity of the textile matrix that has been predetermined to bind 90% of the platelets. To predetermine the extent of binding, a sample of matrix is incubated with excess platelets (more than enough to saturate the matrix) and the amount of platelets left in the mixture after the matrix is removed is calculated.

(c) The matrix is removed from the PRP and the platelet concentration in the residual fluid is measured.

(d) The textile is incubated in a 10× volume of citrated saline for 5 min on a rocker and excess fluid is drained. This step is repeated three times. The soaked textile matrix is then placed in an appropriate volume of citrated saline for a bound textile platelet count of $8\times10^9$ platelets/ml for use in the crosslinking step described below.

(e) 3.5 ml of fixative solution is dropwise added to 1.25 ml soaked platelet-matrix (at $8 \times 10^9$ platelets/ml) with gentle swirling to mix. The mixture is further diluted to a final volume of 10 ml with a faster addition of fixative solution for a final bound textile platelet count of $1 \times 10^9$ platelets/ml. Incubation is performed for 1 hr at room temperature without stirring or agitation. Finally, the platelet-textile matrix is diluted into a ten volumes of imidazole buffered saline and incubated for 5 min on a rocker, and excess fluid is drained off. This step is repeated three times.

(f) To include thrombin, excess imidazole buffered saline is removed from the platelet-textile matrix as thoroughly as possible and then soaked in excess Ia serum as described above. Excess Ia serum is removed and the textile matrix is frozen and lyophilized as described above.

(g) Characterize the freeze-dried hemostatic matrix using thrombin generation analysis (described below).

It will be appreciated by those of skill in the art that although Examples 8 and 9 utilize Textile 1 above to prepare one embodiment of the present invention, any textile combination described herein may alternatively be used (e.g., textiles 2-7 described above).

Thrombin Generation Analysis

This procedure follows Fischer, T. H. et al. Synergistic platelet integrin signaling and factor XII activation in poly-N-acetyl glucosamine fiber-mediated hemostasis. *Biomaterials* 26, 5433-43 (2005). Briefly, the kinetics of thrombin generation can be used to reflect the ability of hemostatic matrixes to function as a catalytic surface for components (e.g., factor XII) of the coagulation cascade. In this assay, thrombin (IIa) cleaves the non-fluorescent synthetic substrate peptide-D-Phe-Pro-Arg-ANSNH to generate a fluorescent product. The timecourse for fluorescence generation is followed in a 96-well fluorescent platelet reader in kinetic mode.

96 well plates are blocked with 150 µl 5% BSA and citrated saline overnight at 37° C., then stored at 4° C. until use. 4 mm (approx.) diameter pieces of hemostatic matrix are prepared with a 4 mm Trephine punch or razor or sharp scissor. Fluorometric IIa substrate D-Phe-Pro-Arg-ANSNH (Cat #SN-17a-$C_6H_{11}$ from Haematologic Technologies, Inc., Essex Junction, Vt.) is diluted 1/200 into plasma, followed by $CaCl_2$ to a final concentration of 10 mM. The mixtures are placed into a fluorometer and fluorescence (490 nm) measured for approximately two hours. Data are analyzed by plotting the timecourse from each well, and measuring the initial and maximal slope of the relative fluorescence change curve and the time required to obtain the maximal slope. The initial and maximal slopes, together with the time to maximal slope, are the quality metrics. The higher the slopes and the shorter the time to maximal slope the more pro-hemostatic the matrix.

Example 10

Preparation of a Dual Fiber Textile

This Example illustrates preparation of a textile made from glass fibers in combination with another selected textile fiber. Two lines of evidence point towards continuous filament glass thread as being a potential component of a hemostatic textile. First, platelets were found to activate and adhere to glass (Barr, H. *Lancet* 238, 609-610 (1941)). As a consequence, glass vessels are generally avoided in the in vitro handling of platelets, and binding to glass is a longstanding method for assessing platelet activity (McPherson, J. & Zucker, M. B. *Blood* 47, 55-67 (1976); Tsukada, T. & Ogawa, T. *Rinsho Ketsueki* 14, 777-84 (1973); Cooper, R. G., Cornell, C. N., Muhrer, M. E. & Garb, S. *Tex Rep Biol Med* 27, 955-61 (1969)). Secondly, plasma proteins (Stouffer, J. E. & Lipscomb, H. S. *Endocrinology* 72, 91-4 (1963); Lissitzky, S., Roques, M. & Benevent, M. T. *C R Seances Soc Biol Fil* 154, 396-9 (1960); Bull, H. B. *Biochim Biophys Acta* 19, 464-71 (1956)), FXII (Ratnoff, O. D. & Rosenblum, J. M. *Am J Med* 25, 160-8 (1958)) and fibrinogen (Sit, P. S. & Marchant, R. E. *Thromb Haemost* 82, 1053-60 (1999); Rapoza, R. J. & Horbett, T. A. *J Biomed Mater Res* 24, 1263-87 (1990); Perez-Luna, V. H., Horbett, T. A. & Ratner, B. D. *J Biomed Mater Res* 28, 1111-26 (1994)) being well-studied examples, undergo chemical and physical adsorption processes on foreign surfaces (Silberberg, A. *J Physical Chem.* 66, 1872-1883 (1962)). FXII (Hageman Factor) was found to be particularly important because it initiates the humoral coagulation at the glass/blood interface (Ratnoff, supra; Ratnoff, O. D. & Margolius, A., Jr. *Trans Assoc Am Physicians* 68, 149-54 (1955)). Platelet activation and turnover of the intrinsic coagulation are highly interrelated mechanisms, in part due to the role platelets play as a catalytic surface for assembly of the Va/Xa complex for thrombin generation. Platelet activation by biomaterials (e.g., via integrin outside-in signaling) can result in surface presentation of phosphatidylserine, an important component of catalytic complexes for thrombin generation (Fischer, T. H., Connolly, R., Thatte, H. S. & Schwaitzberg, S. S. *Microsc Res Tech* 63, 168-74 (2004)). Factor XII has been found to be peripherally associated with the platelet surface for activation of the intrinsic coagulation pathway in the microenvironment of the cell (Iatridis, P. G., Ferguson, J. H. & Iatridis, S. G. *Thromb Diath Haemorrh* 11, 355-71 (1964); Shibayama, Y., Reddigari, S. & Kaplan, A. P. *Immunopharmacology* Vol. 32 24-7 (1996)), although the series of proteolytic steps involving factor XII that occurs on the platelet surface are poorly understood. The net effect of the close relationship between XIIa-mediated coagulation and platelet activation is synergism for earlier initiation of fibrin polymerization.

The interaction of fluids with glasses are largely controlled by surface tension phenomena related to hydrophobicity, zeta potential and wettability. There is minimal interaction of fluids with the interior of the filaments. Thus, a second type of more absorptive fiber was sought to compensate for the low fluid transport and absorptivity of glass. A panel of natural and synthetic fibers was tested for tendency to activate platelets and the intrinsic coagulation cascade. A dual fiber product consisting of continuous filament type E-glass and specialty rayon specialty rayon was prepared and tested for hemostatic effectiveness in porcine models for hemorrhage.

Materials Type E continuous filament glass (ECDE 11.6 fiberglass) was provided by Carolina Narrow Fabrics, Inc. (Winston-Salem, N.C.). Specialty rayon made from bamboo (Bambusa textilis) and other natural and synthetic fibers were provided by Cheraw Yarn Mills, Inc. (Cheraw, S.C.). The dual fiber glass/specialty rayon textile fabric was prepared by Carolina Narrow Fabrics, Inc. (Winston-Salem, N.C.). Gauze was sourced from Kendall (Mansfield, Mass.).

Platelet rich Plasma Isolation Peripheral blood from consenting normal volunteers was drawn into citrate anti-coagulant, then platelet rich plasma was isolated with differential centrifugation as detailed in Fischer, T. H. et al. *Biomaterials* 26, 5433-43 (2005). The platelet concentration in the platelet rich plasma was measured with a Hiska haematological analyzer, and the platelet concentration was adjusted to 150,000 platelets/ul by diluting the sample with platelet free plasma.

Thrombin Generation Kinetics The effect fibers on the kinetics of thrombin generation in platelet rich plasma (at 150,000 platelets/ul) was investigated by following the hydrolysis of the thrombin substrate D-Phe-Pro-Arg-AN- SNH to yield a fluorescent reaction product. 300 ug of each fiber was tested in 100 ul platelet rich plasma in triplicate with the fluorogenic substrate D-Phe-Pro-Arg-ANSNH. The timecourse for thrombin generation was initiated by adding $CaCl_2$ for 10 mM to each sample. The lag time for thrombin generation was defined as the time point at which the fluorescence increased 10% over the initial baseline value.

Thromboelastography Thromboelastographic (TEG) measurements were performed with a TEG-5000 Thrombelastograph Hemostasis Analyzer (Haemoscope Corporation, Niles, Ill.). The assays were initiated by adding $CaCl_2$ to 10 mM to platelet rich plasma (at 150,000 platelets/ul) and then immediately transferring 327 ul of the calcified platelet rich plasma to the thromboelastography chamber that contained the materials in 33 ul citrated saline. The final fiber concentration was 3.0 mg/ml. Measurements were performed for one hour in triplicate at 37° C., and then relevant parameters were extracted from the "stiffness" curve.

Scanning Electron Microscopy SEM analysis on glucosamine-based materials was performed as follows. Whole peripheral blood from normal human volunteers was allowed to flow directly from the venapuncture butterfly onto the dual-fiber textile or gauze so that 1 cm×1 cm of each material was covered by 2 ml of whole blood. The materials were allowed to incubate for one minute, then diluted to 50 ml with citrated saline+1 mM EGTA to quench hemostatic processes. The materials were allowed to settle for 5 min with gravity, then rediluted with citrated saline. This process was repeated two more times to obtain each material free of unbound RBCs. After one-minute contact with blood and the multiple cycles of dilution and material/RBC complex settling, glutaraldehyde was added for 0.1% (w/v) and the samples were allowed to incubate at room temperature for one hour. The samples were diluted 1/1 (v/v) with 4% paraformaldehyde for a final concentration of 2%, and then additional glutaraldehyde was added for a final concentration of 0.5%. The initial stabilization step with 0.1% glutaraldehyde has been shown to minimize osmotically driven alterations in red blood cell (RBC) morphological due to paraformaldehyde exposure (Fischer, T. H. et al. *Microsc Res Tech* 65, 62-71 (2004)). Samples were stored at 4° C. overnight and then examined with a Cambridge S200 scanning electron microscope at 20 kv.

Measurement of Bound RBCs—10 mg samples of dual fiber or gauze were directly exposed to 1.0 ml whole peripheral blood and washed as detailed for scanning electron microscopy. The pGlcNAc were then placed in 10 ml distilled water with 1% TX-100 to release hemoglobin from bound RBCs. The samples were centrifuged at 10,000×g for five minutes, then the absorbance at 414 nm was measured to quantify the total amount of hemoglobin (and thus number of RBCs) associated with each material.

Measurement of Extent of RBC Lysis Due to Material Contact 10 mg samples of dual fiber or gauze were exposed to 1.0 ml whole peripheral blood as in the last two sections. After one minute of exposure, the samples were centrifuged at 10,000×g for five minutes to pellet blood cells and other materials. The optical density at 414 nm was measured to quantify the amount of released hemoglobin in the supernatants, and thus the amount of shed blood.

Porcine Brachial Plexis and Femoral Artery Transection Hemorrhage Model 40 to 50 kg mixed breed pigs are anesthetized with isofluorane and then several sensors are placed to follow hemodynamic and vasoactive processes: a pulmonary artery thermo dilution catheter is inserted via the external jugular vein into a pulmonary artery; micromanometer-tipped catheters are positioned via the left femoral vessels into the right atrium and thoracic aorta; a 22 gauge catheter is inserted into the left femoral artery and connected to a withdrawal pump; catheters are positioned via the left femoral vessels.

The hemorrhage-challenge phase of the experiment was performed in two phases. First, the transactional laceration of contralateral brachial arteries was performed. The brachial arteries and two associated ~3 mm diameter veins were surgically exposed. One each side the artery and two veins were completely transected with a single scalpel stroke. Injuries were established in a near simultaneous manner, and then each side was immediately packed with the dual fiber textile or gauze. The penetrating cut-down sites were completely packed with each material and then pressure was held for six minutes. Packing was removed and the amount of shed blood was ascertained as described below. Both wounds were then repacked with the dual fiber material to stabilize the animals. The second phase of the experiment proceeded by surgically exposing contralateral the femoral arteries. The two contralateral femoral arteries were transected in a near-simultaneous manner and then the surgical sites were packed with dual fiber textile or gauze. Pressure was held for six minutes, then materials were removed for shed blood determination.

The amount of blood shed into the original packing materials were measured by placing the dual fiber or gauze into one liter of distilled water to lyse RBCs. After two hours of stirring at room temperature and storage at 2° C. the optical density at 414 nm was measured to determine the amount of released hemoglobin, and thus the number of shed RBCs and volume blood loss.

Results

Experiments proceeded in three stages. First, candidate materials for formulating the hemostatic textile were identified by measuring the ability of selected fibers to activate hemostatic processes in platelet rich plasma. Secondly, a dual fiber combination was subjected to TEG and SEM analysis to gain insight into the mechanism of function. Finally, the ability of the dual fiber textile to provide hemostasis with porcine hemorrhage models was assessed. Details of these experiments follow.

Figure 1:
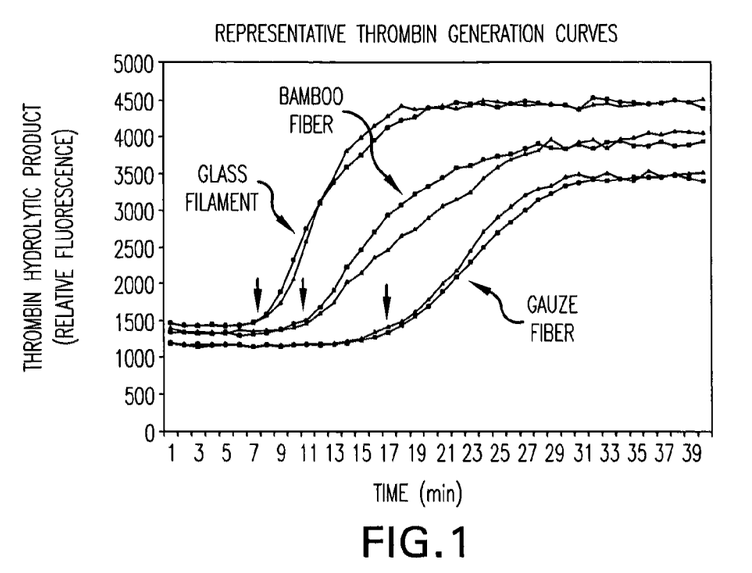
FIG. 1 shows representative thrombin generation curves using one embodiment of the present invention.

Activation of Hemostatic System by Candidate Fibers A panel of common textile fibers were analyzed for their ability to activate platelets and accelerate turnover of the intrinsic (contact) coagulation pathway. The behavior of the representative fibers in the fluorogenic thrombin generation assay is depicted in FIG. 1. In FIG. 1, duplicate samples of glass, specialty rayon or gauze fibers were placed in platelet rich plasma that contained a fluorogenic thrombin substrate and then the thrombin generation timecourse was initiated by adding calcium. Arrows indicate the times for thrombin generation. As shown in FIG. 1, exposure of the platelet rich plasma to type E continuous filament glass resulted in thrombin generation in approximately eight minutes. Specialty rayon was less prothrombogenic with thrombin generation occurring in 12 minutes, while gauze fiber was considerably slower.

Figure 2:
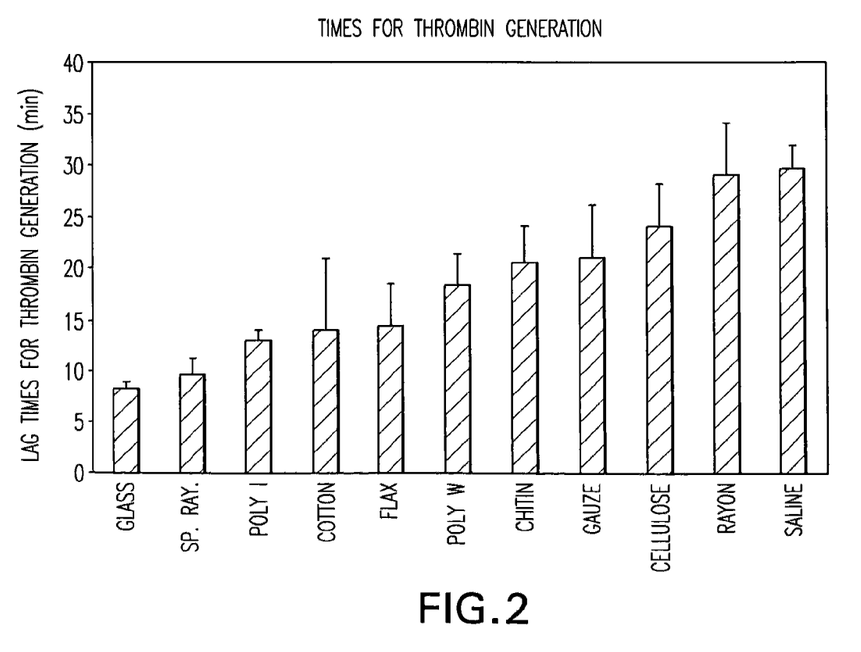
FIG. 2 shows times for thrombin generation using embodiments of the present invention.

The behavior of a more expansive panel of fibers is presented in FIG. 2. In FIG. 2, the indicated fibers were tested as detailed in FIG. 1 to measure times for thrombin generation. Error bars represent the standard deviation of duplicate analysis. As shown in FIG. 2, glass and specialty rayon were respectively the first and second most thrombogenic material tested. Chitin and gauze, which are components of products for surface hemostasis, did not strongly accelerate thrombin generation. A prototype bandage was thus constructed from glass and specialty rayon.

Figure 3:
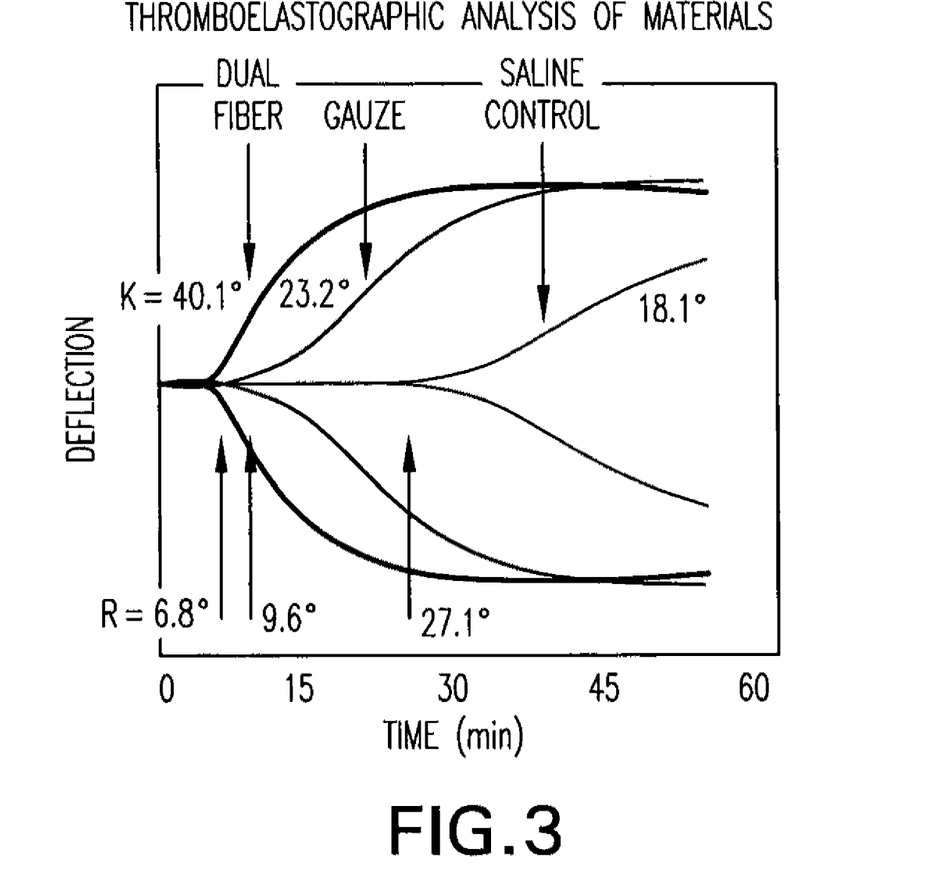
FIG. 3 shows thromboelastographic analysis of materials according to the present invention.
Figure 4:
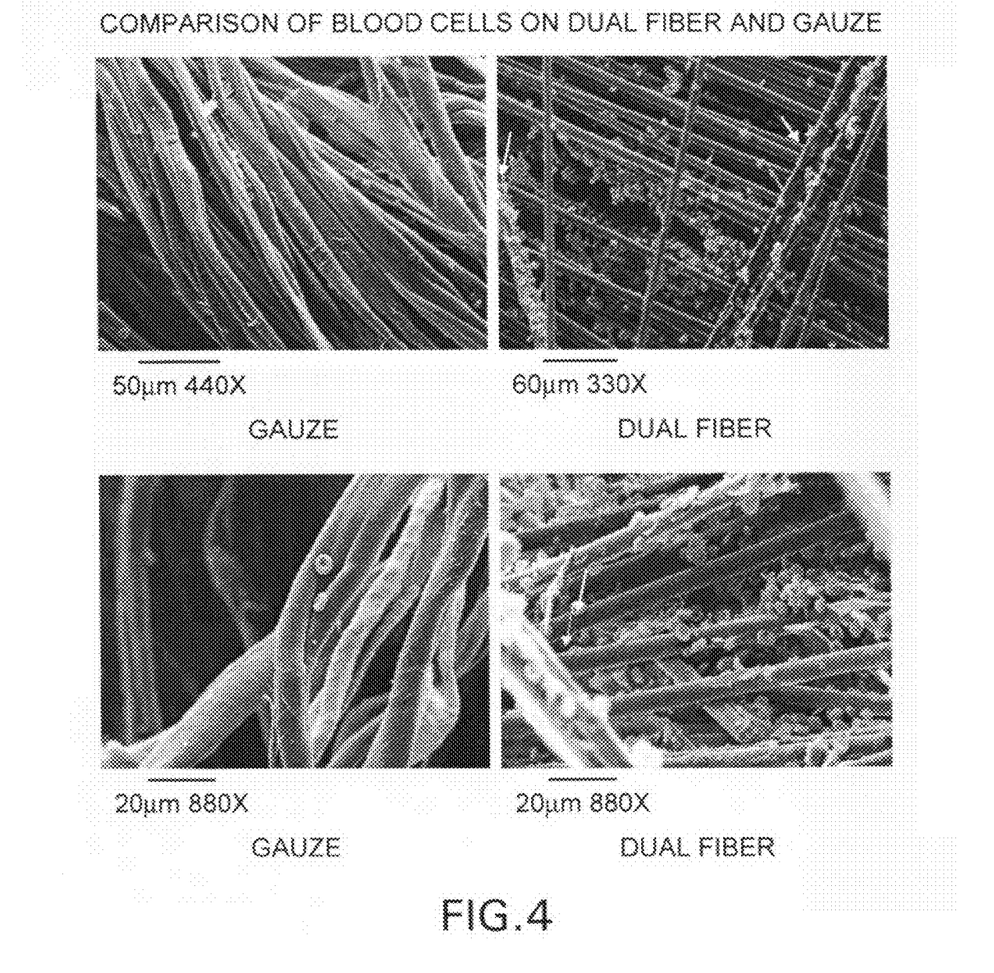
FIG. 4 shows a comparison of blood cells on dual fiber and gauze.

In Vitro Properties of the Glass/Specialty Rayon Dual Fiber Textile The dual-fiber matrix and gauze were compared in the thromboelastographic analysis with platelet rich plasma depicted in FIG. 3. In FIG. 3, dual fiber or gauze were placed in the thromboelastographic cuvette with normal saline and then platelet rich plasma and calcium were added to initiate the clot formation timecourse. Normal saline without material was run as a negative control. As shown in FIG. 3, the glass/specialty rayon textile was found to significantly accelerate fibrin clot formation as compared to gauze or the saline control. Analysis of the dual fiber matrix and gauze after contact with excess peripheral blood was performed using scanning electron microscopy as shown in FIG. 4. In FIG. 4, dual fiber or gauze was saturated with excess peripheral blood and then examined with scanning electron microscopy as detailed above. White arrows in the left two dual fiber panels indicate specialty rayon fibers. As shown in FIG. 4, the glass/specialty rayon matrix tightly bound significant numbers of RBCs, while these cells only sparsely covered the gauze matrix.

Figure 5:
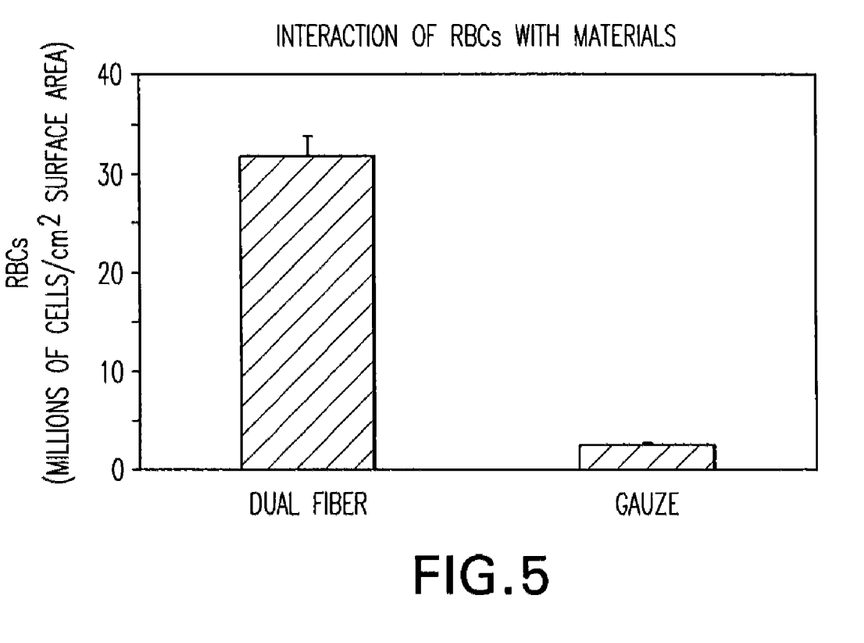
FIG. 5 shows the interaction of red blood cells (RBCs) with materials according to the present invention.
Figure 6:
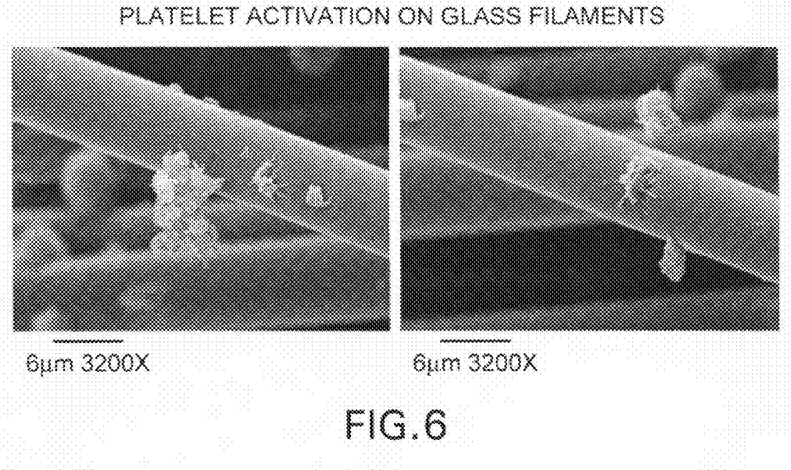
FIG. 6 shows platelet activation on glass filaments used in the present invention.

Quantification of the number of RBCs on each matrix is shown in FIG. 5. In FIG. 5, dual fiber or gauze was saturated with excess peripheral blood, and then the number of bound RBCs was measured as described above. Error bars represent the standard deviation from duplicate measurements. As shown in FIG. 5, the dual fiber textile bound approximately ten times as many RBCs as gauze. Significant lysis of RBCs did not occur (data not shown). SEM examination of the dual fiber matrix also showed a large number of highly activated platelets on the continuous glass filament component, as shown in FIG. 6, which shows dual fiber saturated and washed with peripheral blood and examined with scanning electron microscopy. These results indicate that the glass/specialty rayon matrix is more effective at providing surface hemostasis than gauze.

Figure 7:
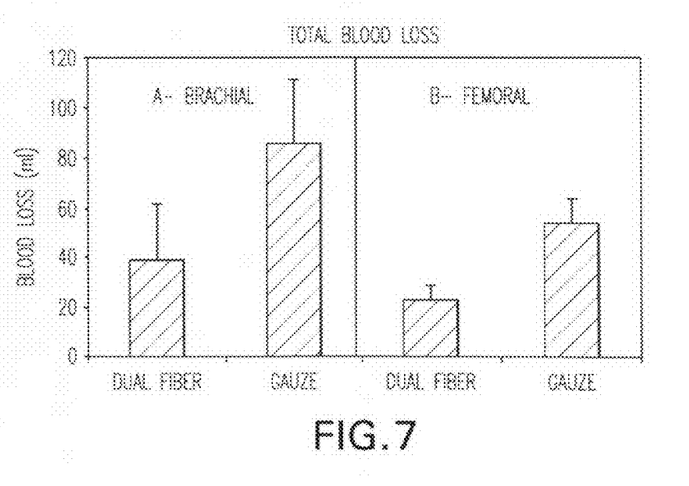
FIG. 7 shows total blood loss using the materials of the present invention.

Ability of the Dual Fiber Bandage to Provide Hemostasis in Porcine Models The dual fiber matrix was compared to gauze in severe porcine large vessel transection injuries. Two types of injuries were established on each of four pigs. First, the brachial artery and two associated large veins in contralateral plexus areas were completely transected in a near-simultaneous manner. This gives an exsanguinating hemorrhage that is both arterial and venous in nature. The contralateral cut-down/injury sites were immediately packed with as much dual fiber textile or gauze as required to fill the injury site. Pressure was then held for six minutes, and then the sites were unpacked and the degree of hemostasis was judged as complete (with no visible hemorrhage), partial (with less than three ml of blood loss per minute) or uncontrolled (with more than three ml of blood loss per minute). The blood loss onto packing materials and any shed blood was measured from each wound site. The contralateral brachial plexus injury sites were then re-packed with dual fiber textile so as to stabilize the animal for the second set of femoral injuries. Contralateral femoral arteries were exposed, and then completely transected in a near simultaneous manner to initiate an exsanguinating hemorrhage. As with the brachial plexus injuries, the injury sites were immediately packed with dual fiber textile or gauze. After holding pressure for six minutes the sites were unpacked and the degree of hemostasis was judged as described for the brachial injuries. An important feature of this large vessel transection model is that the animals were not in hemorrhagic shock. Because the injuries were immediately packed with pressure, the mean arterial pressure was maintained in the 45 to 55 mm Hg range and total blood loss was not more than ~5% of the total blood volume. The total amount of blood loss with the dual fiber material was approximately half as with gauze with both brachial plexus and femoral injuries as shown in FIG. 7. In FIG. 7, the total amount of material-absorbed and shed blood from the six minute pressure period was measured from the brachial (Left Panel A) and femoral (Right Panel B). Error bars represent the standard deviation of the blood loss from similar injuries in five animals. As shown in FIG. 7, there was a marked tendency for gauze to pull off the hemostatic plug (to the extent that there was one), while the dual fiber textile did not strongly incorporate into the hemostatic zone.

The above results show that fundamental principles of hemostasis can be used to design economical materials for surface hemostasis. The glass/specialty rayon textile outperformed gauze in porcine models of both capillary and large vessel injury; bleed times and blood loss were reduced by approximately halve when the fiber component of the textile was optimized with respect to thrombogenicity.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A hemostatic textile, comprising:
   a material comprising glass fibers and raw or regenerated bamboo fibers co-woven or knitted together, wherein the relative amounts of said glass fibers and said raw or regenerated bamboo fibers range from about 0.1% to about 99.9% by weight glass fibers and from about 99.9% to about 0.1% by weight raw or regenerated bamboo fibers, based on the total weight of said textile; and
   thrombin or a fraction comprising thrombin;
   said hemostatic textile capable of activating hemostatic systems in the body when applied to a wound.

2. The hemostatic textile of claim 1, wherein said fraction comprising thrombin further comprises one or more coagulation factors selected from the group consisting of factor XII, factor XIIa, factor XI, factor XIa, factor XIII, factor XIIIa, factor IX, factor IXa, factor VIII, factor VIIIa, factor vWF, factor V, factor Va, factor X, factor Xa, and combinations thereof.

3. The hemostatic textile of claim 1, wherein said fraction further comprises a vasoactive agent.

4. The hemostatic textile of claim 3, wherein said vasoactive agent is selected from the group consisting of endothelins, thromboxanes, NO scavengers, and combinations thereof.

5. The hemostatic textile of claim 1, further comprising a preservative selected from the group consisting of glycerol, propanediol, polyoxyethylene glycol (PEG), trehalose, and combinations thereof.

6. The hemostatic textile of claim 1, wherein said fraction comprising thrombin is a partially purified plasma fraction containing thrombin IIa.

7. The hemostatic textile of claim 1, wherein the relative amounts of said glass fibers and said raw or regenerated bamboo fibers range from about 30% to about 80% by weight glass fibers and from about 70% to about 20% by weight raw or regenerated bamboo fibers, based on the total weight of said textile.

8. The hemostatic textile of claim 1, wherein the relative amounts of said glass fibers and said raw or regenerated bamboo fibers range from about 50% to about 80% by weight glass fibers and from about 50% to about 20% by weight raw or regenerated bamboo fibers, based on the total weight of said textile.

9. The hemostatic textile of claim 1, wherein said thrombin or a fraction comprising thrombin comprises from about 0.01% to about 10% by weight, based on the total weight of said textile.

10. The hemostatic textile of claim 1, wherein said thrombin or a fraction comprising thrombin comprises from about 0.05% to about 7% by weight, based on the total weight of said textile.

11. The hemostatic textile of claim 1, wherein said thrombin or a fraction comprising thrombin comprises from about 0.1% to about 5% by weight, based on the total weight of said textile.

12. The hemostatic textile of claim 1, further comprising one or more additional agents selected from the group consisting of skin conditioners, anti-inflammatory agents, analgesics, antimicrobial or antifungal agents, vasoconstrictors, growth factors, anti-scar agents, cauterizing agents, dehydrating agents, prothrombotic agents, and combinations thereof.

13. The hemostatic textile of claim 1, wherein said textile material is in a woven form.

14. The hemostatic textile of claim 1, wherein said hemostatic textile is an article of clothing or a liner for an article of clothing.

15. A hemostatic textile, comprising:
a material comprising a combination of about 65% by weight glass fibers and about 35% by weight raw or regenerated bamboo fibers, based on the total weight of said textile wherein the glass fibers and the raw or regenerated bamboo fibers are co-woven or knitted together; and
from about 0.1% to about 5% by weight of thrombin or a fraction comprising thrombin based on the total weight of said textile;
said hemostatic textile capable of activating hemostatic systems in the body when applied to a wound.

16. A hemostatic textile, comprising:
a material comprising glass fibers and raw or regenerated bamboo fibers co-woven or knitted together, wherein the relative amounts of said glass fibers and said raw or regenerated bamboo fibers range from about 0.1% to about 99.9% by weight glass fibers and from about 99.9% to about 0.1% by weight raw or regenerated bamboo fibers, based on the total weight of said textile; and
one or more hemostatic agents selected from the group consisting of rehydrated lyophilized (RL) platelets, RL blood cells, fibrin, and fibrinogen;
said hemostatic textile capable of activating hemostatic systems in the body when applied to a wound.

17. The hemostatic textile of claim 16, further comprising one or more coagulation factors selected from the group consisting of factor XII, factor XIIa, factor XI, factor XIa, factor XIII, factor XIIIa, factor IX, factor IXa, factor VIII, factor VIIIa, factor vWF, factor V, factor Va, factor X, factor Xa, and combinations thereof.

18. The hemostatic textile of claim 16, further comprising a vasoactive agent.

19. The hemostatic textile of claim 18, wherein said vasoactive agent is selected from the group consisting of endothelins, thromboxanes, NO scavengers, and combinations thereof.

20. The hemostatic textile of claim 16, further comprising a preservative selected from the group consisting of glycerol, propanediol, polyoxyethylene glycol (PEG), trehalose, and combinations thereof.

21. The hemostatic textile of claim 16, wherein the relative amounts of said glass fibers and said raw or regenerated bamboo fibers range from about 30% to about 80% by weight glass fibers and from about 70% to about 20% by weight raw or regenerated bamboo fibers, based on the total weight of said textile.

22. The hemostatic textile of claim 16, wherein the relative amounts of said glass fibers and said raw or regenerated bamboo fibers range from about 50% to about 80% by weight glass fibers and from about 50% to about 20% by weight raw or regenerated bamboo fibers, based on the total weight of said textile.

23. The hemostatic textile of claim 16, wherein said RL platelets or said RL blood cells comprise from about 0.1% to about 20% by weight, based on the total weight of said textile.

24. The hemostatic textile of claim 16, wherein said fibrin or fibrinogen comprises from about 0.1% to about 5% by weight, based on the total weight of said textile.

25. The hemostatic textile of claim 16, further comprising one or more additional agents selected from the group consisting of skin conditioners, anti-inflammatory agents, analgesics, antimicrobial or antifungal agents, vasoconstrictors, growth factors, anti-scar agents, cauterizing agents, dehydrating agents, prothrombotic agents, and combinations thereof.

26. The hemostatic textile of claim 16, wherein said textile material is in a woven form.

27. The hemostatic textile of claim 16, wherein said hemostatic textile is an article of clothing or a liner for an article of clothing.

28. A hemostatic textile, comprising:
a material comprising a combination of about 65% by weight glass fibers and about 35% by weight raw or regenerated bamboo fibers, based on the total weight of said textile, wherein the glass fibers and the raw or regenerated bamboo fibers are co-woven or knitted together; and
one or more hemostatic agents selected from the group consisting of rehydrated lyophilized (RL) platelets, RL blood cells, fibrin, and fibrinogen, wherein said RL platelets and said RL blood cells comprise from about 0.1% to about 20% by weight and said fibrin and said fibrinogen comprise from about 0.1% to about 5% by weight, based on the total weight of said textile;
said hemostatic textile capable of activating hemostatic systems in the body when applied to a wound.

29. A hemostatic textile, comprising:
a material comprising glass fibers and raw or regenerated bamboo fibers co-woven or knitted together, wherein the relative amounts of said glass fibers and said raw or regenerated bamboo fibers range from about 0.1% to about 99.9% by weight glass fibers and from about 99.9% to about 0.1% by weight raw or regenerated bamboo fibers, based on the total weight of said textile; and
thrombin or a fraction containing thrombin; and
one or more hemostatic agents selected from the group consisting of rehydrated lyophilized (RL) platelets, RL blood cells, fibrin, and fibrinogen;
said hemostatic textile capable of activating hemostatic systems in the body when applied to a wound.

30. The hemostatic textile of claim 29, wherein said fraction further comprises one or more coagulation factors selected from the group consisting of factor XII, factor XIIa, factor XI, factor XIa, factor XIII, factor XIIIa, factor IX, factor IXa, factor VIII, factor VIIIa, factor vWF, factor V, factor Va, factor X, factor Xa, and combinations thereof.

31. The hemostatic textile of claim 29, wherein said fraction further comprises a vasoactive agent.

32. The hemostatic textile of claim 31, wherein said vasoactive agent is selected from the group consisting of endothelins, thromoboxanes, NO scavengers, and combinations thereof.

33. The hemostatic textile of claim 29, further comprising a preservative selected from the group consisting of glycerol, propanediol, polyoxyethylene glycol (PEG), trehalose, and combinations thereof.

34. The hemostatic textile of claim 29, wherein said fraction comprising thrombin is a partially purified plasma fraction containing thrombin IIa.

35. The hemostatic textile of claim 29, wherein the relative amounts of said glass fibers and said raw or regenerated bamboo fibers range from about 30% to about 80% by weight glass fibers and from about 70% to about 20% by weight raw or regenerated bamboo fibers, based on the total weight of said textile.

36. The hemostatic textile of claim 29, wherein the relative amounts of said glass fibers and said raw or regenerated bamboo fibers range from about 50% to about 80% by weight glass fibers and from about 50% to about 20% by weight raw or regenerated bamboo fibers, based on the total weight of said textile.

37. The hemostatic textile of claim 29, wherein said thrombin or a fraction comprising thrombin comprises from about 0.01% to about 10% by weight, based on the total weight of said textile.

38. The hemostatic textile of claim 29, wherein said thrombin or a fraction comprising thrombin comprises from about 0.05% to about 7% by weight, based on the total weight of said textile.

39. The hemostatic textile of claim 29, wherein said thrombin or a fraction comprising thrombin comprises from about 0.1% to about 5% by weight, based on the total weight of said textile.

40. The hemostatic textile of claim 29, wherein said RL platelets or said RL blood cells comprise from about 0.1% to about 20% by weight, based on the total weight of said textile.

41. The hemostatic textile of claim 29, wherein said fibrin or fibrinogen comprises from about 0.1% to about 5% by weight, based on the total weight of said textile.

42. The hemostatic textile of claim 29, further comprising one or more additional agents selected from the group consisting of skin conditioners, anti-inflammatory agents, analgesics, antimicrobial or antifungal agents, vasoconstrictors, growth factors, anti-scar agents, cauterizing agents, dehydrating agents, prothrombotic agents, and combinations thereof.

43. The hemostatic textile of claim 29 in a woven form.

44. The hemostatic textile of claim 29, wherein said hemostatic textile is an article of clothing or a liner for an article of clothing.

45. A hemostatic textile, comprising:
a textile material comprising a combination of about 65% by weight glass fibers and about 35% by weight raw or regenerated bamboo fibers, based on the total weight of said textile wherein the glass fibers and the raw or regenerated bamboo fibers are co-woven or knitted together;
from about 0.1% to about 5% by weight of thrombin or a fraction comprising thrombin based on the total weight of said textile; and
one or more hemostatic agents selected from the group consisting of rehydrated lyophilized (RL) platelets, RL blood cells, fibrin, and fibrinogen, wherein said RL platelets and said RL blood cells comprise from about 0.1% to about 20% by weight and said fibrin and said fibrinogen comprise from about 0.1% to about 5% by weight, based on the total weight of said textile;
said hemostatic textile capable of activating hemostatic systems in the body when applied to a wound.

* * * * *

UNITED STATES PATENT AND TRADEMARK OFFICE
CERTIFICATE OF CORRECTION

PATENT NO. : 8,277,837 B2
APPLICATION NO. : 11/650670
DATED : October 2, 2012
INVENTOR(S) : Thomas H. Fischer Page 1 of 1

It is certified that error appears in the above-identified patent and that said Letters Patent is hereby corrected as shown below:

First Page Col. 2 (Other Publications) Line 9 Delete "Dec. 2003;;" and insert --Dec. 2003;--, therefor.

First Page Col. 2 (Abstract), Line 7 Delete "lyocel" and insert --lyocell--, therefor.

Column 18, Line 50 In Claim 4, delete "thromoboxanes," and insert --thromboxanes,--, therefor.

Column 19, Line 62 In Claim 19, delete "thromoboxanes," and insert --thromboxanes,--, therefor.

Column 21, Line 3 In Claim 32, delete "thromoboxanes," and insert --thromboxanes,--, therefor.

Column 22, Line 21 In Claim 45, after "textile" insert --,--.

Signed and Sealed this
First Day of January, 2013

David J. Kappos
*Director of the United States Patent and Trademark Office*